United States Patent [19]
Meneghin

[11] Patent Number: 5,089,613
[45] Date of Patent: Feb. 18, 1992

[54] PROCESS FOR THE DIRECT AND REGIOSELECTIVE FUNCTIONALIZATION IN POSITION 2 OF PHENOTHIAZINE

[75] Inventor: Mariano Meneghin, Revine-Lago, Italy

[73] Assignee: Zambon Group S.p.A., Vicenza, Italy

[21] Appl. No.: 680,942

[22] Filed: Apr. 5, 1991

[30] Foreign Application Priority Data

Apr. 9, 1990 [IT] Italy .................. 19976 A/90
Jul. 26, 1990 [IT] Italy .................. 21073 A/90

[51] Int. Cl.$^5$ ............... C07D 279/20; C07D 279/30; C07D 45/06
[52] U.S. Cl. ......................... 544/35; 544/39
[58] Field of Search ..................... 544/39, 35

[56] References Cited

U.S. PATENT DOCUMENTS

| | | | |
|---|---|---|---|
| 3,136,762 | 6/1964 | Mayer et al. | 260/243 |
| 3,413,290 | 11/1968 | Renz | 544/39 |
| 3,625,963 | 7/1971 | Lalanne | 544/39 |
| 3,787,413 | 1/1974 | Naka | 544/39 |
| 3,961,055 | 6/1976 | Baget | 424/247 |

FOREIGN PATENT DOCUMENTS 1314521 5/1963 France.
1480553 7/1977 United Kingdom.

OTHER PUBLICATIONS

Duperray Chemical Abstracts, 59, 6418b (1963).

*Primary Examiner*—Mark L. Berch
*Attorney, Agent, or Firm*—Stevens, Davis, Miller & Mosher

[57] ABSTRACT

Preparation of 2-alkylthio-phenothiazines by direct functionalization of phenothiazine by reaction of the phenothiazine, N-protected by an acryl group, with a sulfonating agent such as sulfuric acid, sulfuric anhydride, chlorosulfonic acid, or oleum, in order to obtain, after work-up of the reaction mixture, phenothiazine-2-sulfonic acid, followed by the reduction of this or, optionally, of its acyl chloride derivative, to obtain 2-mercapto-phenothiazine which subsequently is subjected to S-alkylation to thereby obtain the desired target compound.

7 Claims, No Drawings

PROCESS FOR THE DIRECT AND REGIOSELECTIVE FUNCTIONALIZATION IN POSITION 2 OF PHENOTHIAZINE

The present invention relates to a process for the preparation of 2-alkylthio-phenothiazines, which are useful as intermediates for the preparation of drugs.

2-Alkylthio-phenothiazine of formula

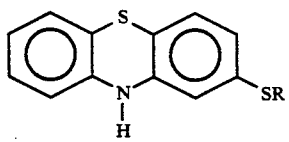

wherein R is a $C_1$–$C_4$ alkyl group; are known intermediates for the preparation of compounds with pharmaceutical activity among which Thioridazine (Merck Index, XI Ed., No. 9290, page 1474)

Mesoridazine (Merck Index, XI Ed., No. 5813, page 929)

Methiomeprazine (Merck Index, X Ed., No. 5847, page 857)

Thiethylperazine (Merck Index, XI Ed., No. 9241, page 1467)

may be cited.

The compounds of formula I are also intermediates for the synthesis of some of the compounds with contraceptive activity described in U.S. Pat. No. 4,578,379 and for the synthesis of some of the compounds useful as stabilizers for hydrocarbons described in the Japanese patent application No. 48-28761 [Yoshitomi—(C.A. 81:15387c)].

Several processes for the preparation of the compounds of formula I are known but, however, they often show negative features which make them not very suitable from an industrial point of view. Such negative features include a long synthesis which needs a high number of steps and the separation and purification of the intermediates, starting materials which are not available on the market or available only at high cost, reactants and catalysts of difficult industrial use, low yields or again the formation of by-products of difficult separation.

As an example of the several methods in the literature, the following may be cited: a three-steps synthesis starting from a condensation between 3-methylthioaniline and 2-chloro-benzoic acid which provides compound I (R=CH$_3$) with the 4-methylthio isomer as an impurity (Helvetica Chimica Acta, 41, 1063, 1958); a four-steps synthesis which requires by first a condensation between sodium 2-bromothiophenate and 2-chloro-5-methylthio-nitrobenzene or the condensation between 2-chloro-thiophenol and 2-bromo-5-methylthio-nitrobenzene [Swiss patent No. 404,669, Sandoz—(C.A. 65:15392h)], or the condensation between 4-methylthio-thiophenol and 2-chloro-nitrobenzene to obtain 2-nitro-4'-methylthio-diphenylsulfide, its reduction in autoclave at 70 atmospheres, a diazotization and a reaction with decalin of the thus obtained azide [Japanese patent application No. 16283/62, Yoshitomi—(C.A. 59:11516e)].

British patent No. 863,547 [Sandoz—C.A. 55:19962d)] describes the preparation of compound I (R=CH$_3$) by reacting N-(3-methylthio-phenyl)-aniline with sulfur in the presence of iodine. However, the aniline-derivative must be synthesized separately. Other examples of preparation of phenothiazines are collected in Heterocycles, vol. 26, No. 1, page 239, (1987).

As far as we know, processes for the preparation of 2-alkylthio-phenothiazines which use as starting material phenothiazine, a compound available on the market in industrial amounts and at low cost have never been disclosed.

We have now found and it is the object of the present invention a process for the preparation of 2-alkylthio-phenothiazines which comprises the direct functionalization of phenothiazine by regioselective introduction in position 2 of an SH group from which the desired product is obtained by alkylation.

Such process comprises the reaction of the phenothiazine N-protected by an acyl group, with an equimolecular or preferably an excess of a sulfonating agent selected among sulfuric acid, sulfuric anhydride, chlorosulfonic acid or oleum, in order to obtain, after work-up of the reaction mixture, phenothiazine-2-sulfonic acid. The reduction of this or, optionally, of its acyl chloride derivative, in order to obtain 2-mercapto-phenothiazine, and the subsequent S-alkylation, allow to prepare 2-alkylthio-phenothiazine.

The process object of the present invention uses products and reactants of low cost and of easy industrial use and it provides the desired compound with good yields and with high purity.

The starting product of the process is an N-acyl-derivative of phenothiazine.

Such derivative can be represented by the following general formula

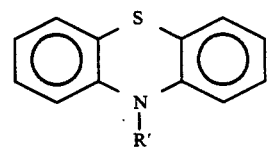

wherein R' is an acyl group of a $C_1$–$C_6$ aliphatic carboxylic acid or of benzoic acid and, preferably, it is a formyl, acetyl or benzoyl group.

The compounds of formula II are prepared by acylating phenothiazine with acyl halides or anhydrides or, optionally, also with formic acid according to known techniques.

A great number of the compounds of formula II are already known and, in particular, the preferred compounds are described in the following papers:

N-formyl-phenothiazine [Austral. J. Chem., 8, 252, (1955)]

N-acetyl-phenothiazine (Liebigs Ann., 230, 95)

N-benzoyl-phenothiazine [Berichte, 18, 1843–49, (1885)].

The sulfonation of compound II, carried out with the above indicated specific sulfonating agents, provides the N-acyl-phenothiazine-2-sulfonic acid of formula

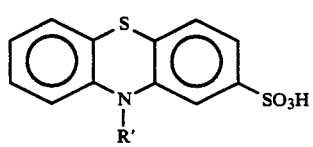

The sulfonation reaction is carried out without solvent or in the presence of an inert solvent selected among methylene chloride, 1,2-dichloro-ethane, sulfurous anhydride, nitrobenzene, nitromethane, sulfuryl fluoride and acetic acid.

Compound III can be isolated as such or as a salt, for example, as an alkaline salt.

The preparation of the alkaline salt is carried out according to known techniques, for example, by using alkaline bases.

The thus obtained compound III, or its alkaline salt, can be optionally converted into the acyl chloride derivative of formula

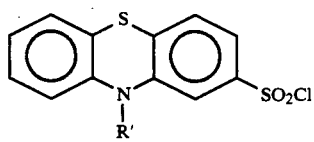
(III-A)

by known techniques.

In particular, chlorinating agents such as, for example, thionyl chloride, phosphorous pentachloride, phosphoryl chloride, are used. The reaction is carried out in the presence of an inert solvent selected among methylene chloride, toluene, 1,2-dichloro-ethane, tetrachloro-ethane, chlorobenzene and, optionally, of a catalytic amount of dimethylformamide (5–10%).

The preferred chlorinating agent is thionyl chloride.

The reduction of compound III as such or, optionally, the reduction of its acyl chloride derivative of formula III-A, provides 2-mercap-to-phenothiazine of formula

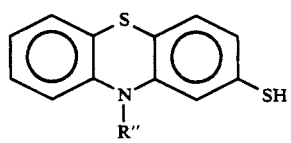
(IV)

wherein R" is hydrogen or an acyl group.

The reduction reaction is carried out according to conventional techniques suitable to reduce the sulfur atom.

A method, which affords good results with low industrial cost, consists in carrying out the reduction with zinc in acid environment. Alternatively, the reduction of compound III-A is carried out with catalytic amounts of iodides in the presence of sodium metabisulfite in order to obtain the disulfide of formula

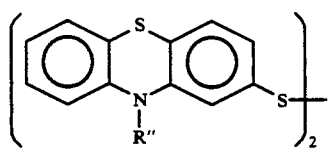
(V)

wherein R" has the above meanings; which is then further reduced to the corresponding mercapto-derivative (compound IV) with suitable reducing agents such as, for example, zinc in hydrochloric acid, zinc in acetic acid, zinc in sulfuric acid, tin in hydrochloric acid, aluminum in acetic acid, sodium or potassium sulfide in hydroalcoholic environment or by electrochemical reduction.

Preferably, the thus obtained compound IV is not isolated but directly alkylated in the same reaction environment in order to obtain the compounds of formula I. This reaction is known per se and it is carried out by using normal alkylating agents of industrial use which depend on the nature of the alkyl group to be introduced, such as, for example, dimethyl-sulfate, methyl chloride, diethyl-sulfate. It is possible, for example, to prepare 2-methylthio-phenothiazine, an intermediate useful for the synthesis of Thioridazine (Merck Index, XI Ed., No. 9290, page 1474) or to prepare 2-ethylthio-phenothiazine useful for the synthesis of a drug known as Thiethylperazine (Merck Index, XI Ed., No., 9241, page 1467).

The most typical and innovating aspect of the present process is the sulfonation step of phenothiazine II which affords compound III or, after work-up of the reaction mixture, compound III-A, with good yield and with a practically complete regioselectivity of the attack in position 2.

In fact, the used reaction conditions allow to obtain a practically total monosubstitution in position 2 of the phenothiazine ring.

The presence of the 2,8-disubstituted by-product is reduced to very small amounts (lower than 5%) and, therefore, it is practically absent or easily removable by known techniques.

In particular, the preferred reaction conditions are those in which the sulfonation reaction is carried out with sulfuric acid at 96% or chlorosulfonic acid.

The sulfonation reaction is carried out without solvent or in the presence of an inert solvent such as, for example, methylene chloride, 1,2-dichloro-ethane, and by working at a temperature comprised between $-20°$ C. and 80° C. and, preferably, between 15° C. and 40° C.

Preferably, before reduction, the thus obtained phenothiazine-2-sulfonic acid of formula III is directly transformed into its sulfonyl chloride derivative according to above described known techniques. In particular, the sulfonyl chloride derivative is obtained by adding, directly to the same sulfonation environment, thionyl chloride in the presence of an inert organic solvent such as, for example, methylene chloride, 1,2-dichloro-ethane and of a catalytic amount of dimethylformamide.

The chlorination reaction gives high yields (higher than 95%). The reduction step of compound III-A to compound IV is, preferably, carried out with zinc in hydrochloric or sulfuric acid and, practically, it can be carried out by adding to the organic solution of compound III-A the acid and, then, zinc.

Again, the reduction step can be carried out with water and sodium metabisulfite in the presence of catalytic amounts of sodium iodide and of a quaternary ammonium salt.

The disulfide V is obtained and easily reduced according to known techniques.

The mercapto-derivative (IV) is preferably alkylated in the same reduction environment with dimethylsulfate in order to obtain compound I ($R=CH_3$).

Alternatively, N-acyl-phenothiazine-2-sulfonic acid is transformed into its sodium salt, by using, for example, sodium hydroxide and, then, chlorinated according to the above indicated procedures.

It is clear to the man skilled in the art that during the steps of the process object of the present invention, N-deacylation may occur.

In this case, the nitrogen atom of phenothiazine can be optionally protected again in the similar way to what above indicated.

In a practical embodiment, the process object of the present invention consists in carrying out the sulfonation step of N-formyl-phenothiazine with chlorosulfonic acid in a molar amount about 2–5 times higher than the substrate to be sulfonated.

The sulfonation reaction is carried out in the presence of an inert organic solvent, for example methylene chloride, and at a temperature comprised between 15° and 40° C.

The thus obtained N-formyl-phenothiazine-2-sulfonic acid is directly chlorinated with thionyl chloride in the presence of catalytic amounts of dimethylformamide.

The thus obtained acyl chloride derivative of formula III-A is reduced with zinc in the presence of hydrochloric acid or sulfuric acid and, then, directly methylated with dimethylsulfate, in the presence of an organic inert solvent such as, for example, methylene chloride, in order to obtain the 2-methylthio-phenothiazine of formula I ($R=CH_3$).

Another practical embodiment of the process object of the present invention consists in carrying out the sulfonation step with sulfuric acid at 96% in a molar amount at least 20 times higher than the substrate and working in the same above indicated reaction conditions in order to obtain compound I.

The process object of the invention shows various advantages with respect to the processes of the prior art.

Such advantages, whose industrial usefulness is clear to the man of the art, can be summarized in the low cost of the starting materials, in their easy availability in industrial amounts, in the reduced number of steps (N-acylation of phenothiazine, sulfonation and reduction in the same reaction environment with contemporaneous deprotection, S-alkylation) in the easy industrial application of the above steps, in the high regioselectivity of the process and in the remarkably higher global yield than that obtainable by the known methods.

In order to better illustrate the present invention the following examples are now given.

The HPLC analysis was carried out according to the following parameters:

Instrument: Waters 600E
Detector: Waters 484 UV (254 nm)
Column: Merck RP-8
Injected volume: 5 μl
Flow: 1.5 ml/minute
Temperature: 50° C.
Eluent phase: a gradient of the following two solutions:
 A) $KH_2PO_4$ 0.02M pH 3 buffer
 B) $CH_3CN$/Isopropanol=2.3/2.2
according to the following scheme:

| | |
|---|---|
| from time 0 minutes to time 4 minutes | 70% A/30% B |
| from time 4 minutes to time 8 minutes gradient up to | 55% A/45% B |
| from time 8 minutes to time 16 minutes | 55% A/45% B |
| from time 16 minutes to time 17 minutes gradient up to | 70% A/30% B |
| from time 18 minutes to time 20 minutes | 70% A/30% B |
| Retention times: | |
| N-formyl-phenothiazine-2-sulfonic acid | 2.37 minutes |
| N-formyl-phenothiazine-2-sulfonyl chloride | 12.20 minutes |

EXAMPLE 1

Preparation of N-formyl-phenothiazine-2-sulfonic acid

Method A

1) Into a reactor, equipped with mechanical stirrer and thermometer, chlorosulfonic acid (17.49 g) and, slowly under stirring, N-formyl-phenothiazine (7.5 g) were charged, under nitrogen at 20° C. The reaction mixture was left under stirring at 20° C. for 3 hours. The HPLC analysis showed the formation of N-formyl-phenothiazine-2-sulfonic acid (75% yield).

2) Into a 50 ml double-jacket reactor, equipped with mechanical stirrer, reflux condenser and thermometer, methylene chloride (18 g) and N-formyl-phenothiazine (10 g) were charged under nitrogen. The thus obtained suspension was cooled to 15° C. and chlorosulfonic acid (15.38 g) was added under stirring in 30 minutes. At the end of the addition, the reaction mixture was heated up to 35° C. and it was kept at this temperature for 4 hours.

The HPLC analysis showed the formation of N-formyl-phenothiazine-2-sulfonic acid (80% yield).

Method B

Into a reactor, equipped with mechanical stirrer and thermometer, acetic acid (26.25 g) and 20% oleum (47.47 g) were charged at 20° C. under nitrogen.

N-formyl-phenothiazine (5.0 g) was added to the mixture. The temperature was carried to 50° C. and the reaction mixture was left under stirring at this temperature for 1.5 hours.

The HPLC analysis showed the formation of N-formyl-phenothiazine-2-sulfonic acid (54% yield).

EXAMPLE 2

Preparation of sodium phenothiazine-2-sulfonate

Into a 700 ml reactor, equipped with mechanical stirrer and thermometer, 96% sulfuric acid (920 g; 9 mol) was charged and it was heated up to 30° C.

Then, N-formyl-phenothiazine (50 g; 0.22 mol) was added portionwise in about 10 minutes.

The reaction mixture was left in inert atmosphere, under stirring at 30° C. for 22 hours.

At the end, in 10–15 minutes, under good stirring and keeping the temperature below 90° C., the solution was poured into a beaker containing deionized water (1300 g) and equipped with mechanical stirrer and thermometer.

The mixture was kept under stirring at 90° C. for one hour. By cooling at room temperature, a crystalline precipitate was obtained. Then, methylene chloride (530 g) was added and the reaction mixture was stirred for 30 minutes.

The product of the sulfonation reaction can be isolated according to two different procedures:

A) At 30°–35° C., 30% sodium hydroxide (2120 g) was added to the reaction mixture until neutrality. A solid separated.

The suspension was left under stirring at 20° C. for one hour, then the solid was filtered and put into a beaker equipped with mechanical stirrer and containing deionized water (5000 g).

The suspension was stirred for 1.5 hours at room temperature. At the end, the solid was filtered and dried at 80° C.

Sodium phenothiazine-2-sulfonate was obtained (60 g; 63% yield) (HPLC titre 70%, the remaining are inorganic salts).

B) Celite (10 g) was added to the mixture. The mixture was cooled under stirring to 0° C. and then filtered.

The thus obtained solid was treated with deionized water (500 g) for one hour at 70° C.

At the end, the insoluble was filtered and washed with hot deionized water (100 g).

To the filtrate, 30% sodium hydroxide (195.7 g) was added and the pH was carried to 12.5.

The thus obtained suspension was left under stirring for one hour, then it was filtered at room temperature.

The insoluble was washed with a saturated NaCl solution (2×60 g). The thus obtained solid was dried under vacuum at 80° C.

Sodium phenothiazine-2-sulfonate was obtained (62 g; 65% yield) (HPLC titre 70%; the remaining are inorganic salts).

EXAMPLE 3

Preparation of sodium N-formyl-phenothiazine-2-sulfonate

Into a 500 ml reactor, equipped with mechanical stirrer and thermometer, under nitrogen flow, 99% formic acid (311 g) and, under good stirring, crude sodium phenothiazine-2-sulfonate (50 g), prepared as described in example 2, were charged.

Keeping under stirring, acetic anhydride (55.7 g) was added dropwise in 15 minutes. At the end of the addition, the temperature was 40° C. The mixture was left under stirring for 18 hours, then the solvent was evaporated to dryness at reduced pressure and at 60° C.

The thus obtained solid was suspended in toluene (200 ml) and then it was filtered.

The insoluble was dried under vacuum in oven at 80° C. for 12 hours. The crude sodium N-formyl-phenothiazine-2-sulfonate (55.7 g) was obtained.

EXAMPLE 4

Preparation of N-formyl-phenothiazine-2-sulfonyl chloride

Method A

The reaction mixture containing N-formyl-phenothiazine-2-sulfonic acid, prepared according to method A(1) of example 1, was directly diluted with methylene chloride (20 ml). The solution was treated with thionyl chloride (5.5 g) in the presence of a catalytic amount of dimethylformamide.

The HPLC analysis showed the formation of N-formyl-phenothiazine-2-sulfonyl chloride (96% yield).

Method B

Dimethylformamide (0.16 g) and, in 20 minutes, thionyl chloride (6.8 g) were directly added to the reaction mixture containing N-formyl-phenothiazine-2-sulfonic acid, prepared according to method A(2) of example 1.

The mixture was left at 35° C. for 9 hours.

The HPLC analysis showed the formation of N-formyl-phenothiazine-2-sulfonyl chloride (96% yield).

Method C

Into a 700 ml double-jacket reactor, equipped with mechanical stirrer, reflux condenser and thermometer, methylene chloride (463.8 g) and crude sodium N-formyl-phenothiazine-2-sulfonate (55.7 g), prepared according to example 3, were charged under nitrogen flow.

Dimethylformamide (0.61 g) was added to the thus obtained suspension.

It was carried to reflux under stirring and, then, a solution of thionyl chloride (22.9 g) in methylene chloride (99.4 g) was added dropwise in 15 minutes.

At the end of the addition, the reaction mixture was refluxed for 15 hours. Then it was left to cool at room temperature and, then, filtered on celite.

The celite was washed with methylene chloride (2×67 g) and then the solvent was evaporated.

N-formyl-phenothiazine-2-sulfonyl chloride was obtained which was used as such for the subsequent reaction.

EXAMPLE 5

Preparation of 2-methylthio-phenothiazine

Into a 100 ml double-jacket reactor, equipped with magnetic stirrer and thermometer, deionized water (25 g) and 96% sulfuric acid (8.2 g) were charged under nitrogen flow.

The solution was cooled to 0° C. and a solution of crude N-formyl-phenothiazine-2-sulfonyl chloride (5.3 g), prepared as described in example 4, in methylene chloride (20 g) was added under stirring. To this mixture, kept under stirring at 0° C., zinc powder (4.01 g) was added portionwise in 30 minutes.

At the end of the addition, the mixture was left at 0° C. for 30 minutes and, then, the temperature was left to rise up to room vlaue. The mixture was left under nitrogen and under stirring overnight. Then, it was refluxed for 2 hours at 40° C.

At the end, it was cooled to 15° C. with water and filtered on celite. Celite was washed with methylene chloride (13 g) and the filtrate was poured into a 100 ml separatory funnel.

The organic phase was separated, washed with hydrochloric acid 6N (22 g) and added dropwise into a 100 ml reactor containing aqueous 5% sodium hydroxide (40 g), under stirring at 0° C. and under inert atmosphere.

The phases were separated always at 0° C.

The aqueous phase was charged into a four-necked 250 ml flask equipped with mechanical stirrer, thermometer and pH-meter.

Dimethylsulfate (1 g) was added dropwise to the solution, under slow stirring, in nitrogen atmosphere and keeping the temperature at 0° C. The reaction mixture was stirred at 0° C. for 30 minutes, neutralized with concentrated hydrochloric acid and filtered.

The thus obtained solid was washed with water and dried under vacuum at 80° C.

2-methylthio-phenothiazine (2 g) was obtained.

EXAMPLE 6

Preparation of di-(2-phenothiazinyl)-disulfide

Into a double-jacket reactor, equipped with magnetic stirrer and thermometer, a solution of N-formyl-phenothiazine-2-sulfonyl chloride (5.6 g) in methylene chloride (66.3 g) was charged under nitrogen.

To the solution, tricaprylylmethylammonium chloride [a compound commercialized by General Mills Inc. with the trade name "Aliquat 336"] (0.5 g) and aqueous hydriodic acid (acidimetric titre 57%, 0.2 g) in deionized water (20 ml) were added.

The mixture was left under stirring at room temperature and a solution of sodium metabisulfite (4.5 g) in deionized water (10 ml) was added dropwise in 5 minutes.

The thus obtained mixture was left under nitrogen and under stirring for one hour.

Then, it was poured into a 100 ml separatory funnel.

The organic phase was separated and the aqueous phase was extracted with methylene chloride (2×30 g).

The collected organic phases were washed with water, dried and the solvent was evaporated at reduced pressure.

An oily residue (7.2 g) consisting of N,N'-di-formyl-di-(2-phenothiazinyl)-disulfide and di-(2-phenothiazinyl)-disulfide was obtained.

By reduction with zinc in hydrochloric acid and treatment with sodium hydroxide, 2-mercapto-phenothiazine was obtained.

What we claim is:

1. A process for the preparation of 2-alkylthiophenothiazines by direct functionalization of phenothiazine which comprises reacting a phenothiazine N-protected by an acyl group having the formula

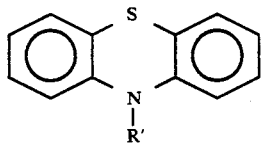

(II)

wherein R' is an acyl group of a $C_1$–$C_6$ aliphatic carboxylic acid or of benzoic acid, with a sulfonating agent selected from the class consisting of sulfuric acid, sulfuric anhydride, chlorosulfonic acid, and oleum in order to obtain, after work-up of the reaction mixture, a phenothiazine-2-sulfonic acid, reducing this or, optionally, its acyl chloride derivative, to obtain 2-mercapto-phenothiazine, and subsequently S-alkylating this last to thereby obtain the desired target compound.

2. A process according to claim 1 wherein the phenothiazine N-protected by a formyl group is treated with sulfuric acid or chlorosulfonic acid in order to obtain N-formyl-phenothiazine-2-sulfonic acid which is directly chlorinated in the same sulfonation environment with thionyl chloride, then reduced with zinc in acid environment and directly methylated.

3. A process according to claim 1 wherein the phenothiazine N-pro-tected by an acyl group is selected the class consisting of N-formyl-phenothiazine, N-acetyl-phenothiazine and N-benzoyl-phenothiazine.

4. A process according to claim 1 wherein the sulfonating agent is selected the class consisting of sulfuric acid and chlorosulfonic acid.

5. A process according to claim 1 wherein the reduction reaction is carried out with zinc in acid environment.

6. A process according to claim 1 wherein 2-mercapto-phonethiazine is directly methylated thus obtaining 2-methylthio-phenothiazine.

7. A process according to claim 1 wherein 2-mercapto-phonethiazine is directly ethylated thus obtaining 2-ethylthio-phenothiazine.

* * * * *